(12) United States Patent
Johnston et al.

(10) Patent No.: US 6,221,620 B1
(45) Date of Patent: Apr. 24, 2001

(54) MONOCLONAL ANTIBODIES SPECIFIC FOR HUMAN THYMIDYLATE SYNTHASE

(75) Inventors: Patrick G. Johnston, Bethesda; Carmen J. Allegra, Gaithersburg; Bruce A. Chabner, Potomac; Chi-Ming Liang, Bethesda, all of MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 07/690,841

(22) Filed: Apr. 24, 1991

(51) Int. Cl.$^7$ .............................. C07K 1/00; C07H 21/02
(52) U.S. Cl. ............... 435/7.23; 435/172.2; 435/240.27; 435/810; 436/513; 436/548; 436/611; 436/813; 436/164; 436/169; 436/170; 436/518; 436/805; 530/350; 530/806; 530/388.26; 530/388.8; 536/23.2; 536/23.7
(58) Field of Search .......................... 435/7.23, 4, 172.2, 435/240.27, 810, 189, 172.3, 69.1, 325, 69.7, 375, 7.1, 372.3, 30, 240.2, 320.1, 252, 70.3, 366, 33, 7.21, 91.33, 235.1, 69.4, 320, 240.11, 240.21, 3, 14, 34, 176; 436/513, 548, 64, 813, 164, 169, 170, 518, 805; 530/388.26, 388.8, 350, 806; 536/23.2, 23.7

(56) References Cited

PUBLICATIONS

Rode, W., et al., "Purification of Mammalian Tumor (L1210) Thymidylate Synthetase by Affinity Chromatography on Stable Biospecific Adsorbent," *The Journal of Biological Chemistry*, 254(22) :11538–11543 (Nov. 25, 1979).

Brown, G. & N.R. Ling "Murine monoclonal antibodies" Ch3 in *Antibodies vol. I* D. Catty Ed, IRL Press 1988 pp. 81–104.*

Jastreboff, M.M. et al. "Isolation and Functional Effects of Monoclonal Antibodies Binding to Thymidylate Synthase" 1985 Biochemistry 24:587.*

Navalgund, L.G. et al. "Cell Cycle Regulation of Thymidylate Synthetase Gene Expression in Cultured Mouse Fibroblasts" 1980 J. Biol. Chem. 255(15):7386.*

* cited by examiner

Primary Examiner—Jennifer Graser
Assistant Examiner—Lisa V. Daniels-Cook
(74) Attorney, Agent, or Firm—Townsend and Townsend and Crew LLP (57) ABSTRACT

The present invention relates to monoclonal antibodies that are specific for the protein thymidylate synthase, and hybridomas producing these monoclonal antibodies. The invention further relates to methods of detection and diagnostic kits to test for the presence of thymidylate synthase. The invention also relates to the use of the monoclonal antibodies in determining the presence of colon carcinoma cells.

20 Claims, 8 Drawing Sheets

(3 of 8 Drawing Sheet(s) Filed in Color)

Thymidylate Synthase Level

| Cell line | Absolute Fdump Binding pmol/mg cytosol protein | Relative Fdump Binding | Relative Densitometer Measurement |
|---|---|---|---|
| NCI H630R$_{10}$ | 9.2±0.46 | 36 | 39 |
| NCI H630R$_1$ | 1.58±0.27 | 6 | 10.6 |
| NCI H630W | 0.25±0.02 | 1 | 1 |

MONOCLONAL ANTIBODIES SPECIFIC FOR HUMAN THYMIDYLATE SYNTHASE

BACKGROUND OF THE INVENTION

1. Technical Field

The present invention relates, in general, to monoclonal antibodies and, in particular, to monoclonal antibodies that are specific for thymidylate synthase.

2. Background Information

The fluoropyrimidines are an important group of antineoplastic agents that are widely used in the treatment of gastrointestinal tumors, breast tumors, and epithelial tumors of the upper aerodigestive tract (Danenberg, P. V. (1977) *Biochim. Biophys. Acta Acta* 473, 73–92; Santi, D. V., McHency, C. S. and Sommer, M. (1974) *Biochemistry* 13, 471–480; Moertel, C. G. (1978) *N. Engl. J. Med.* 299, 1049–1052). Thymidylate synthase (TS; EC 2.1.1.45) catalyzes the methylation of deoxyuridine monophosphate (dUMP) to deoxythymidine monphosphate (dTMP). The de novo synthesis of dTMP is an essential step in the synthesis of pyrimidine nucleotides and DNA biosynthesis (Santi, D. V. and Danenberg, P. V. (1984) In *Folates and Pterins*, eds. Blakley, R. L. and Benkovic, S. J. (Wiley, New York), pp. 345–398; Heidelberger, C. (1975) In *Handbook of Experimental Pharmacology*. Vol. 38, eds. Sartorelli, A. C. and Johns, D. G. (Springer Verlag, New York), pp. 193–231). TS enzyme inhibition is one of the main biochemical events underlying the antineoplastic action of the fluoropyrimidines 5-fluorouracil (5-FU) and fluorodeoxyuridine (FUdR). Once metabolized to FdUMP, this metabolite forms a tight-binding covalent complex with TS in the presence of 5-10-methylenetetrahydrofolate ($CH_2H_4PteGlu$).

The TS enzyme exists as a dimer of identical subunis, each 36 kD in size, and has been purified and well characterized from various sources. A striking degree of homology exists between the amino acid sequence of human TS and TS from other sources such as bacteria, parasite and yeast (Hardy, L. W., Finer-Moore, J., Montfort, W., Jones, M., Santi, D. V. and Stroud, R. M. (1987) *Science* 235, 448–4553). Since TS provides the sole de novo source of thymidylate, which is crucial for DNA synthesis, the maximal cellular TS activity occurs during the S phase of the cell cycle and is 20-fold higher in rapidly proliferating cells than in nondividing cells (Conrad, A. H. and Ruddle, F. H. (1972) *J. Cell. Sci.* 10, 471–486; Navalgund, L. G., Rossann, C., Muench, A. J. and Johnson, L. F. (1980) *J. Biol. Chem.* 255, 7386–7390; Johnson, L. F. (1984) In *Recombinant DNA and Cell Proliferation*, eds. Stein, G. S. and Stein, J. L. (Academic Press, New York), pp. 25–47). Moreover, the activity of the TS enzyme increases acutely as a cell passes from late-$G_1$ to early-S phase of the cycle (Jenh, C. H., Rao, L. G. and Johnson, L. F. (1985) *J. Cell. Physiol.* 122, 149–154).

The clinical importance of TS has recently been noted by several investigators who have demonstrated in vivo as well as in vitro that TS enzyme levels in neoplastic cells rise rapidly when cells are exposed to 5-fluorouracil (Spears, C. P., Antranik, A. H., Moran, R. G., Heidelberger, C. and Corbett, T. H. (1982) *Cancer Res.* 42, 450–456; Washtein, W. L. (1984) *Mol. Pharmacol.* 25, 171–177; Chu, E., Zinn, S., Boarman, D. and Allegra, C. J. (1990) Cancer Res. 50, 5834–40; Keyomarsi, K. and Moran, R. G. (1988) *J. Biol. Chem.* 263, 14402–14409; Scanlon, K. J. and Kashani-Sabet, M. (1988) *Proc. Natl. Acad. Sci. USA* 85, 650–653; Swain, S. M., Lippman, M. E., Egan, E. F., Drake, J. C., Steinberg, S. M. and Allegra, C. J. (1989) *J. Clin. Oncol.* 7, 890–896). Thus, the ability of a tumor to acutely overexpress the TS enzyme may play a key role in the development of tumor resistance and may represent an important protective mechanism in response to this drug. Understanding the biochemical and molecular mechanisms involved in antimetabolite resistance both in tumor cell lines and individual patients is critical in assessing and improving chemotherapeutic approaches.

The quantitation and detection of TS in human tissues has traditionally been performed by enzymatic biochemical assays that either measure catalytic activity or measure the amount of radiolabeled FdUMP binding to TS following extraction of the enzyme from cells and tissues (Lockshin, A. and Danenberg, P. V. (1981) *Biochem. Pharmacol.* 30, 247–257; Lockshin, A. and Danenberg, P. V. (1979) *J. Biol. Chem.* 254, 12285–12288). These assays have several limitations when applied to the measurement of TS activity in human tissue samples. While the assays have the required sensitivity for quantitating enzyme in vitro pure populations of malignant cells in culture, they lack adequate sensitivity to measure the lower levels of enzyme activity in human tumors. Previous investigations from our laboratory measuring the TS levels in human breast tumor biopsy specimens revealed that large quantities of tumor (>50 mg) were required to carry out these studies (Scanlon, K. J. and Kashani-Sabet, M. (1988) *Proc. Natl. Acad. Sci. USA* 85, 650–653). Both the catalytic and FdUMP binding assays also require that the enzyme is active; therefore only fresh or frozen tissue can be assayed, thus limiting the assay to prospective studies with the caveat that no enzyme degradation has occurred during the preparation of the samples. In addition, the biochemical assay does not discriminate between areas of the tumor with differing morphologies nor can it measure TS on a cell-to-cell basis. Since tissues and cell preparations are a composite of a heterogenous population, any measurement of TS enzyme using biochemical techniques is confounded by the degree of contamination by cells other than those of interest.

The advent of monoclonal antibody (MoAb) technology has created the opportunity to use monoclonal antibodies as tools in studying the cellular distribution, tissue expression and pharmacokinetics of biologically important molecules. The availability of a monoclonal antibody directed against human TS might provide the adequate sensitivity and specificity needed to overcome those problems inherent in the biochemical assay. In addition, a monoclonal antibody to TS may provide a method for the immunological quantitation of the enzyme in a variety of human tissues and enable analysis to be undertaken on a cell-by-cell basis. This study presents the derivation and characterization of monoclonal antibodies to TS. These antibodies provide a basis for the immunological detection and quantitation of the TS enzyme in human cells, and describe the immunohistochemical localization of the TS enzyme in human colon carcinomas.

The instant invention presents the derivation and characterization of monoclonal antibodies to thymidylate synthase. These antibodies provide a basis for the immunological detection and quantitation of the T.S.enzyme in human cells, and enable the immunohistochemical localization of the T.S. enzyme in human colon carcinomas.

SUMMARY OF THE INVENTION

It is an object of the present invention to provide hybridomas capable of producing monoclonal antibodies specific for antigenic sites on thymidylate synthase.

It is another object of the present invention to provide monoclonal antibodies that recognize antigenic epitopes of thymidylate synthase.

Yet another object of the present invention is to provide a method of immunological detection and quantitation of thymidylate synthase in tissue cells, including tumors (for example, colon carcinomas) in normal and malignant tissue.

It is a further object of the present invention to provide a diagnostic method for the immunological quantitation and detection of thymidylate synthase that does not require large quantities of tissue.

It is yet another object of the present invention to provide a diagnostic method for the immunological quantitation and detection of thymidylate synthase where the tissue architecture will be intact.

It is a further object of the present invention to provide a qualitative method by which to detect changes in the amount of thymidylate synthase present individual cells.

Yet another object of the present invention is to provide a method of detecting thymidylate synthase with adequate sensitivity for both in vitro and in vivo work.

A further object of the present invention is to provide a method for the detection of thymidylate synthase on a cell to cell basis.

In one embodiment, the present invention relates to hybridomas, resulting from the fusion of myeloma cells and spleen cells, which produce monoclonal antibodies specific to thymidylate synthase, where the monoclonal antibodies form an immune complex with antigenic determinants of the T.S. Seven stable hybridomas were produced: TS 102, TS 105, TS 106, TS 109, TS 110, TS 111A and TS 111B. The myeloma cell may be derived from a mouse, and the spleen cell from any mammal, including but not limited to mouse or human. The T.S. has a molecular weight of about 36,000 daltons.

In another embodiment, the present invention relates to monoclonal antibodies specific for antigenic determinants of thymidylate synthase. Further, the monoclonal antibodies may be of classes IgM or IgG.

In a further embodiment, the present invention relates to a diagnostic kit for detecting colon carcinoma comprising in combination:

an insoluble surface or support containing microtiter wells;

thymidylate synthase or antigenic fragments thereof which are bound to the support; and at least one of the above-described monoclonal antibodies, or a binding fragment thereof, which specifically bind to the thymidylate synthase or antigenic fragments thereof; and means for detecting the amount of thymidylate synthase or antigenic fragments thereof in a test which bind to monoclonal antibody or binding fragments.

In another embodiment, the present invention relates to a method for determining the presence of colon carcinoma cells in a biological sample, comprising:

i) contacting the sample with at least one monoclonal antibody specific for an antigenic determinant of thymidylate synthase, under conditions such that binding of monoclonal antibody to antigenic determinant occurs, and ii) detecting the presence or absence of complex formed between the monoclonal antibody and the antigenic determinant.

In another embodiment, the present invention also relates to a diagnostic kit for detecting the presence of thymidylate synthase comprising in combination:

an insoluble surface or support containing microtiter wells;

thymidylate synthase or antigenic fragments thereof which are bound to the support; and at least one monoclonal antibody as described above, or binding fragment thereof, which specifically binds to thymidylate synthase or antigenic fragments thereof; and means for detecting the amount of thymidylate synthase or antigenic fragments thereof in a test which bind to the monoclonal antibody or binding fragments.

In a further embodiment, the present invention also relates to a method of determining the presence of thymidylate synthase in a biological sample, comprising:

i) contacting the sample with at least one monoclonal antibody specific for an antigenic determinant of thymidylate synthase, under conditions such that binding of the monoclonal antibody to the antigenic determinant occurs, and ii) detecting the presence or absence of complex formed between the monoclonal antibody and the antigenic determinant.

BRIEF DESCRIPTION OF THE FIGURES

This application contains at least one drawing excuted in color.

FIG. 4. A. Immunocytochemical staining of NCI-H630-resistant line using TS 106. Cytoprep preparations were made as described in Materials and Methods. Cells were fixed in acetone and stained with the antibodies using the ABC immunoperixidase staining technique. The cells were counterstained in hematoxylin, mounted and coverslipped with permount.

B. Immunocytochemical staining of NCI-H630-sensitive line using TS 106. Cytoprep slides were made with cells in the exponential phase of growth an processed as described above. All resultant staining was examined using an Olympus light microscope.

FIG. 5. A. Western blot analysis for human TS from colon carcinoma cell lysates $NCI-H630_{R1}$ and $NCI-H630_{R10}$ using antibodies TS 106 or TS 109. Cytosolic extracts from cells in the exponential phase of growth were prepared as described in Materials and Methods. Equivalent amounts of protein (100 µg/well) from resistant and sensitive lines were resolved with 15% SDS-polyacrylamide gel, transferred and incubated with TS 106 or TS 109. Staining was performed using horseradish peroxidase-conjugated secondary antibody at a 1/500 dilution.

B. A comparison of the relative and absolute TS levels in the NCi H630$_{R10}$, NCI H630 colon carcinoma cell lines as measured by the biochemical FdUMP binding assay and densitometric quantitation of Western blot analysis as shown in FIG. 5A.

FIG. 6. A. Immunohistochemical staining of a human colon carcinoma tissue specimen using antibody TS 106. Tissue samples obtained from patients were cut and 6 micron sections applied to poly-1-lysine coated slides. The tissue was fixed in acetone and incubated with antibody TS 106 and stained using the ABC immunoperoxidase technique. Tissues were counterstained in hematoxylin, mounted and examined under a light microscope.

B. Immunohistochemical staining of the same sample of fresh-frozen tissue with TS 106 antibody that has been preincubated with rhTS for 30 min prior to application to the tissue. Otherwise the tissue is processed as described above.

DETAILED DESCRIPTION OF THE INVENTION

Thymidylate synthase is an important enzyme that plays a key role in DNA nucleotide precursor synthesis and represents an important therapeutic target for the fluoropyrimidine antineoplastic agents. The present invention relates to monoclonal antibodies specific for antigenic determinants on thymidylate synthase. The invention also relates to hybridoma cell lines that produce the monoclonal antibodies. In a preferred embodiment, the invention relates to any one of the following seven stable hybridoma cell lines that secrete antibodies to thymidylate synthase: TS 102, TS 105, TS 106, TS 109, TS 110, TS 111A and TS 111B. Of the antibodies secreted by these hybridomas, TS 106, TS 109, TS 110 and TS 111A belong to the IgG class, while TS 111B belongs to the IgM class.

Hybridomas, for example, murine hybridomas, that produce monoclonal antibodies that are immunoreactive with the enzyme thymidylate synthase can be prepared and selected for as described in the Examples that follow. For example, mice (i.e. balb/c mice) can be immunized with the thymidylate protein by intraperitoneal injection. After sufficient time has passed to allow for an immune response, the mice can be sacrificed and the spleen cells obtained and fused, advantageously, with myeloma cells, using techniques well known in the art. The resulting fused cells, hybridomas, are then grown in a selective medium, and the surviving cells grown in such medium using limiting dilution conditions. After cloning and recloning, hybridomas can be isolated that secrete antibodies (for example, of the IgG or IgM class) directed to the target, thymidylate synthase, which protein has a molecular weight of 36,000 daltons. Monoclonal antibodies to which the invention relates recognize an antigenic site on thymidylate synthase.

A hybridoma that secretes antibody TS 106 was deposited on Mar. 26, 1998 at the American Type Tissue Culture Collection, 10801 University Boulevard, Manassas, Va. 20110, and was assigned ATCC deposit number HB-12497.

The invention also relates to useful binding fragments of the T.S.-specific monoclonal antibodies, such as Fab or F(ab')$_2$. The antibody fragments can be obtained by conventional techniques, for example, by digestion of the antibody using papain or pepsin.

The present invention also relates to a method of detecting thymidylate synthase. For instance, the presence of thymidylate synthase in a biological sample can be determined by:

i) contacting the sample with at least one monoclonal antibody specific for an antigenic determinant of thymidylate synthase, under conditions such that binding of the monoclonal antibody to an antigenic determinant occurs, and ii) detecting the presence or absence of complex formed between the monoclonal antibody and the antigenic determinant. The present method is advantageous over currently utilized methods for T.S. detection, such as biochemical assays. In order to detect and quantitate T.S. using a biochemical assay, large quantities (>50 mg) of sample tissue are required. In addition, the level of enzyme cannot be measured on a cell to cell basis because it must be extracted from samples as a cytosolic extract. A biochemical assay, while sensitive to enzymes in pure populations of malignant cells, is not sufficiently sensitive to accurately measure T.S. levels in tissue where enzyme activity is low. The present invention is superior over biochemical assays in that substantial quantities of sample tissue are not necessary, enzyme levels can be accurately measured on a cell to cell basis, and there is adequate sensitivity and specificity to detect T.S., even at low activity.

The present invention also relates to a method of determining the presence of tumor cells, for example, colon carcinoma cells, in a biological sample. T.S. plays a crucial role in the in vivo synthesis of DNA, and its maximal cellular activity occurs during the S phase of the cell cycle. As such, T.S. activity is significantly greater in rapidly dividing cells, such as are found in tumors, than in non-dividing cells. Therefore the ability to quantitatively detect the presence of T.S. in vivo may also enable the detection of rapidly dividing cells, including tumors. In one embodiment, this is accomplished by i) contacting the sample with at least one monoclonal antibody specific for an antigenic determinant of thymidylate synthase, under conditions such that binding of the monoclonal antibody to the antigenic determinant occurs, and ii) detecting the presence or absence of complex formed between the monoclonal antibody and the antigenic determinant.

While the above-specified examples of the monoclonal antibodies of the present invention are of the IgG and IgM classes, and are obtained from a murine source, this is not meant to be a limitation. The antibodies of this invention and those functionally equivalent thereto (that is, capable of binding to the above-described T.S. antigens) are within the scope of the invention, whether from a murine source, or other mammal, including human, or combinations thereof. Likewise, antibodies of other classes such as IgA, IgE, etc., and isotypes within the classes, are also within the intended scope of the invention.

Isolation and purification of the monoclonal antibodies can be accomplished using various conventional methods, which free monoclonal antibodies from other proteins and contaminants (see, for example, Goding, in *Monoclonal Antibodies: Principals and Practice*, Chapter 4, 1986)

Another important feature displayed by the monoclonal antibodies of the present invention is their ability to detect T.S. in fresh frozen human colon carcinoma tissues and paraffin embedded tissues. In addition, these antibodies are able to recognize and distinguish completed and uncomplexed proteins, which is important in terms of enzyme inhibition.

The importance of the TS enzyme level as a mechanism of drug resistance is indicated by studies demonstrating that acute induction of TS protein as well as stable amplification of TS may be associated with 5-FU resistance in human breast and colon cancer cell lines (Spears, C. P., Antranik, A. H., Moran, R. G., Heidelberger, C. and Corbett, T. H. (1982) Cancer Res. 42 450–456; Washtein, W. L. (1984) Mol. Pharmacol. 25, 171–177.; Chu, E., Zinn, S., Boarman, D. and Allegra, C. J. (1990) Cancer Res. 50, 5834–40; Keyomarsi, K. and Moran, R. G. (1988) J. Biol. Chem. 263, 14402–14409; Scanlon, K. J. and Kashani-Sabet, M. (1988) Proc. Natl. Acad. Sci. USA 85, 650–653; Bradford, M. (1976) Anal. Biochem. 72, 248–254; Hsu, S. M., Raine, L. and Fanger, H. (1981) J. Histochem. Cytochem. 29, 577–585). The clinical relevance of acute TS induction has been suggested by an in vivo study carried out on tumor biopsy samples obtained from patients with breast carcinoma that documented a 2- to 6-fold increase in TS 24 hours post-fluorouracil therapy (Swain, S. M., Lippman, M. E., Egan, E. F., Drake, J. C., Steinberg, S. M. and Allegra, C. J. (1989) J. Clin. Oncol. 7, 890–896). These in vivo and in vitro studies suggest that the ability of a tumor to overexpress TS in response to cytotoxic agents is important in the clinical development of tumor resistance.

Until now the measurement of TS levels in human tissue has been carried out by using the radiolabeled FdUMP binding assay (Lockshin, A. and Danenberg, P. V. (1981) Biochem. Pharmacol. 30, 247–257; Lockshin, A. and Danenberg, P. V. (1979) J. Biol. Chem. 254, 12285–12288). This assay is performed on a cytosolic extract wherein relatively large quantities of tissue are required and the cellular specificity is lost. The biochemical study assay cannot discriminate between areas of the tumor with differing morphologies, nor can it measure TS on a cell-to-cell basis, and, as tissues and cell preparations are a composite of a heterogenous population, any measurement of TS enzyme is confounded by the degree of contamination by cells other than those of interest. In comparison to the biochemical assay, the availability of a quantitative immunohistochemical assay to measure TS in human cells and tissues is advantageous in the potential examination of cells in tissue sections. Such an assay allows TS measurement in primary and metastatic tumor samples on a cell-by-cell basis, and facilitates detailed correlations between the level of TS and various clinical and morphological parameters. This information can be of value in patient selection for 5-FU treatment. In addition to TS quantitation in tissues and cells, these antibodies will permit accurate studies of TS synthesis and its regulation by drugs such as 5-FU and methotrexate and biologicals such as the interferons, both in vitro and in vivo. Their ability to recognize and distinguish native and complexed protein will help provide information about stability of the TS-FdUMP-folate complex and its modulation by exogenous folates.

In conclusion, the present invention relates to seven monoclonal antibodies to human TS that are highly reactive on immunohistochemical, ELISA, Western and immunoprecipitation studies. Two of these antibodies can be used to detect and quantitate TS in human cells and tissue specimens. The development of a quantitative TS immunohistochemical assay utilizing these antibodies can provide insight into the biological importance of this enzyme and define the clinical relevance of TS.

The ability of a tumor in vitro as well as in vivo to acutely overexpress T.S. in response to cytotoxic agents may play an important role in the development of tumor resistance and thus T.S. overexpression may be of clinical importance. The measurement of T.S. levels in human tissue has until now been carried out by using the radio labelled Fdump binding assay. This assay is performed on a cytosolic extract, large quantities of tissue (>50 mg) are required and the tissue architecture is destroyed. The ability of Mabs TS 106 and TS 109 to localize T.S. in human tissue will allow small (i.e. 6 micron) samples of tissue to be analyzed, the tissue architecture will be intact, and detailed pathological correlations may be made. Thus, an important application of these antibodies will be the immunological detection and quantitation of T.S. in human tumors in an attempt to define the full clinical importance and role of this key peptide.

The invention also relates to a diagnostic kit for detecting the presence of thymidylate synthase, which, in one embodiment, comprises in combination:

an insoluble surface or support containing microtiter wells;

thymidylate synthase or antigenic fragments thereof which are bound to the support at least one monoclonal antibody as described above, or a binding fragment thereof, which specifically binds to the antigenic portions of thymidylate synthase; and means for detecting the amount of antibodies in a test which bind to the monoclonal antibody or binding fragments.

The following non-limiting Examples illustrate the invention in more detail.

EXAMPLE 1

Development and Selection of Hybridomas

Recombinant thymidylate synthase protein was a kind gift from Dr. D. Santi (University of California). Polyethylene glycol was purchased from J. T. Baker. Pristan was purchased from (Aldrich Chemical Co. Wis.). Peroxidase labeled affinity purified goat antimouse immunoglobulins were purchased from (Kirkegaard and Perry Laboratories, Md.). ([6-$^3$H] 5 Fdump 18 ci/mmol) was purchased from Moravek Biochemicals Brea, Calif.) ($^{14}$C Methionine was purchased from NEN Boston, Mass.) 96 well Immulon Plates (Dynatech). A.B.C. Immunoperoxidase kits (Vector Laboratories, California). All other chemicals were obtained from Sigma or NIH supply.

Immunization Fusion and Cloning

Five female balb/c mice (10 weeks old) were injected intraperitoneally with recombinant human thymidylate synthase (r T.S.) 10 ug per mouse. The r T.S. peptide had been emulsified in freund's complete adjuvant. The mice were subsequently boosted twice with r T.S. 10 ug/mouse at 21 day intervals. A mouse with high reactivity ($\geq 1/100,000$ by ELISA) was chosen and injected with r T.S. 10 ug in 0.5 ml phosphate buffer saline 4 days prior to fusion. Spleen cells ($1 \times 10^8$) from the immunized mouse were fused with $2 \times 10^7$ P3×63 Ag 8 variant 653 myeloma cells by using 50% (v/v) polyethylene glycol 3350 (J.T. Baker Chemical Co. N.J.) as a fusing agent. The fusion procedure of Galfre and Milstein was used (Galfre et al., Nature 1977 266:550). The fused cells were plated onto 96 well plates and screened for monoclonal antibody production by ELISA starting on day 28 post fusion. The ELISA-positive hybridomas were cloned and recloned three times at 1.10 and 50 cells per 96-well plates on feeder cells. The resultant stable colonies were expanded into 25 CM$_2$ Falcon Flasks. In this fusion 412 hybridomas resulted from plating of fused cells into 768 wells (53%) ELISA positive clones were detected in 114/412 (27%) wells and 38 of these were positive by subsequent western blot assays. The ELISA positive hybridomas were cloned and recloned by limiting dilution techniques. Seven stable hybridomas were produced which secreted antibodies to thymidylate synthesis. These were identified as TS 102, TS 105, TS 106, TS 109, TS 110, TS 111A and TS 111B.

Preparation and Purification of Ascitic Fluid

The mice were injected intraperitoneally with 0.5 mls of Pristan (Aldrich Chemical Co. Wis.) and 10–14 days later inoculated with 1×10$^6$ hybridoma cells per mouse. The ascitic fluid was collected at 2–3 day intervals until the animal was sacrificed. The ascitic fluid was purified by precipitation with 40% ammonium sulphate and high pressure liquid chromatography (Liang, C.-M., Herren, S., Said, A. and Jost, T. (1985) *Biochem. Biophys. Res. Commun.* 128, 171–178). Isotypic analysis using immunodiffusion techniques indicated that 4 cell lines produced antibodies of the IgG class, and 1 cell line produced antibodies of the IgM class. The class and subclass of the monoclonal immunoglobulins produced were determined by Ouchterlony analysis with antisera specific for u chains and for IgG and IgM subclasses (Ouchterlony O. In Weir D. M. (eds) Handbook of experimental immunology. Oxford and Edinburgh: Blackwell 1976 655–707). Antibodies TS 106, TS 109, TS 110 and TS 111A belonged to the IgG1 class, while antibody TS 111B belonged to the IgM class.

Iodination of Recombinant Human TS Protein $^{125}$I-rhTS was prepared using the purified rhTS protein (EC 2.1.1.45). The soluble lactoperoxidase technique was used to label the rhTS with $^{125}$I (FLPC for Monoclonal Antibody Purification (Pharmacia brochure). The labeled protein was separated from unreacted Na $^{125}$I by passing the iodination mixture through a Sephadex G-25 column, equilibrated and eluted with a buffer containing 0.01 m PBS, pH 7.4, 0.15 m NaCl and 0.1% BSA.

ELISA

An Immulon II (Dynatech) 96 well plate was coated with 50 ul of thymidylate synthase (1 ug/ml) in coating buffer (0.015 M NaHCO$_3$) overnight at 4° C. The wells were then washed thoroughly with PBS/tween (IN PBS, 0.1% Azide 0.05% tween) and incubated with 100 ul of bovine serum albumen 5 mg/ml at room temperature for 1 hour. After washing three times with PBS/tween 50 ul of hybridoma supernatant was added and incubated at room temperature for 2 hours. The unbound antibody was then washed off with three further washes of PBS/tween and 50 ul of alkaline phosphatase conjugated antimouse antibodies were added for 4 hours. The wells were then washed three times in PBS/tween and 50 ul of substrate solution containing (p-Nitrophenyl phosphate (PNP) 40 mg in 20 mls 100 mm NaHCO$_3$, 10 mg MgCl$_2$, pH 8.0) was added to each well. The substrate gave a greenish yellow color and the optical density of the reaction was assessed at 405 mm in a microelisa autoreader (Dynatech). Determination of positive hybridomas cultures was based on signals >0.5 units above background.

EXAMPLE 2

Detection of Antigenic Epitopes

A method of detecting antigenic epitopes recognized by the monoclonal antibodies is to use the sandwich ELISA and study the competition between labeled and unlabeled antibodies.

Preparation of Enzyme Labeled Antibodies

The purified antibodies were conjugated with horseradish peroxidase by the method of Nakane and Kawaoi (Hsu et al., J Histochem Cytochem 1981 29:577–580).

Sandwich ELISA

An immunoplate Immulon II (Dynatech) was coated with unlabeled anti-T.S. antibodies. (10 ug/ml 50 ul/well) at 4° C. overnight and then saturated with BSA 5% (100 ul per plate). After washing with phosphate buffered saline (PBS) pH 7.2 a standard concentration of r T.S. protein was added and incubated for 2 hours at room temperature. The unbound r T.S. protein was washed off and the peroxidase labelled anti-r T.S. antibodies were added for 2 hours at room temperature. The wells were then washed with PBS/tween 0.05%. Fifty microliters of substrate containing 0.1 mg/ul solution of ABTS (2.2 azino-di-3 ethyl-benzthiazoline-6-sulfonic acid) in 50 mm citrate/phosphate buffer 0.01% hydrogen peroxide pH 5.2. Thirty minutes later the optical density of the reactive mixture was measured at 405 mm in a microelisa auto reader (Dynatech).

Antigenic epitopes recognized by the monoclonal antibodies may be distinguished by the sandwich ELISA technique, in which labeled and unlabeled antibodies compete for binding.

T.S. 106 was competed by T.S. 109 and T.S. 110. T.S. 111A was competed by T.S. 109 but not by T.S. 110 or T.S. 106 (Table 1). Monoclonal antibodies TS 106, TS 109, TS 110, TS 111A, and TS 111B, reacted strongly with the recombinant T.S. peptide by ELISA. These results indicate that T.S. 106 and 110 bind to the same epitope while T.S. 111A binds to a separate epitope. T.S. 109 either binds to a region overlapping with the other two sites or binds to both sites respectively.

EXAMPLE 3

Characterization of Monoclonal Antibodies

Characterization of each individual monoclonal antibody including their reactivity in immunoprecipitation and Western Blot, ELISA and isotype is summarized in Table 2.

Western Blot Analysis

A sample of either r T.S. peptide (1 $\mu$g/ml/lane) or cell lysate (200 $\mu$g/well/lane) from two 5-FU resistant cell lines (NCI-H630R$_{10}$, and NCI-H630R$_1$) and a sensitive human colon cell line (NCI-H630) resuspended in 0.1 M K$_2$ PO$_4$ pH 7.4 were run on a 15% SDS-polyacrylamide gel according to the method of Laemmli (Thorell, J. L. and Johnansson, B. G. (1971) *Biochim. Biophys. Acta* 251, 363–369) and electrophoretically transferred onto nitrocellulose membrane (Schleicher and Schuell, New Hampshire) in transfer buffer 948 mm Tris 39 mm glycine, EDTA×2 hours. The nitrocellulose membrane was incubated with a blocking solution (Blotto 5% Carnation nonfat milk, 10 mm. Tris, 0.01% Thimerosol) for 2 hours. The nitrocellulose was then incubated with the T.S. monoclonal antibodies (200 ug/ml). After overnight incubation a horseradish peroxidase conjugated rabbit anti-mouse immunoglobin (Kirkegaard and Perry) was added at (1/500 dilution) for 2 hours. Chromogenic substrate 4 Chloro-1-Napthol (Sigma) was subsequently added and the positive T.S. bands were easily identifiable. Protein concentrations were determined by the Bio-Red protein assay. (Nakane, P. K. and Kawaoi, A. (1974) *J. Histochem. Cytochem.* 22, 1084–1091).

All antibodies displayed a very high ELISA titer, $\geq 1$ in 100,000 with the recombinant T.S. peptide on Western blot analysis revealed that all of the Mabs reacted with the r T.S. peptide band that migrated to approximately 36 KD under denaturing conditions. In addition a second band was observed just below the 36 KD band which presumably is a breakdown product of r T.S (Lockshin, A. and Danenberg, P. V. (1979) *J. Biol. Chem.* 254, 12285–12288). The monoclonal antibodies also displayed reactivity on Western blot analysis of cell lysate extracts from a human colon carcinoma cell line (H630).

Figure 1:
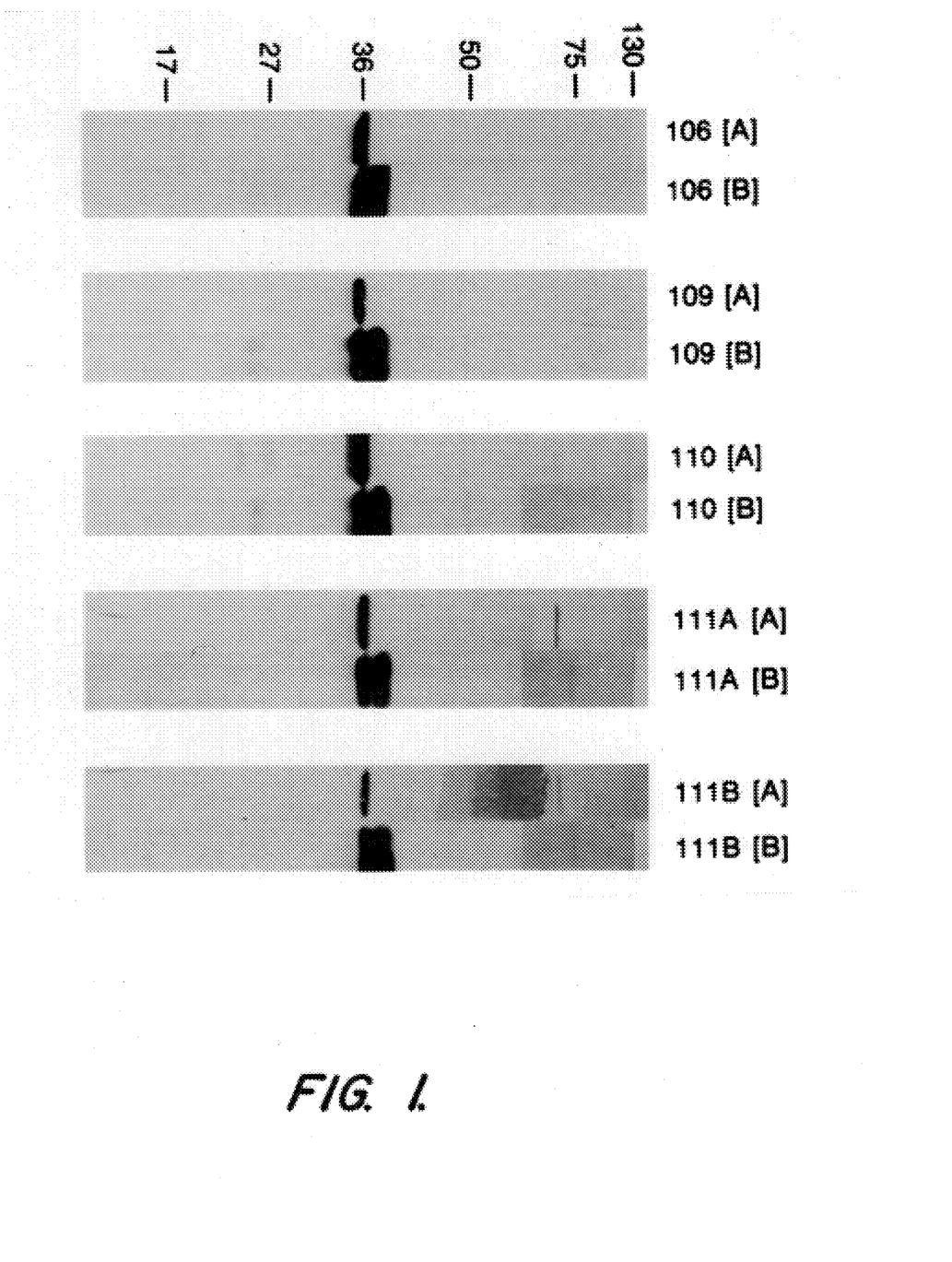
FIG. 1. Western blot analysis of cell lysate from the human colon cell line NCI-H30 that was not exposed to 5-FU (column A) or exposed to 5-FU for 48 hours (column B). Cytosolic extracts from cells in the exponential phase of growth were prepared as described in Materials and Methods. Proteins (100 $\mu$g) were resolved on SDS-polyacrylamide gels, transferred to nitrocellulose and stained with the monoclonal antibodies.
Figure 2:
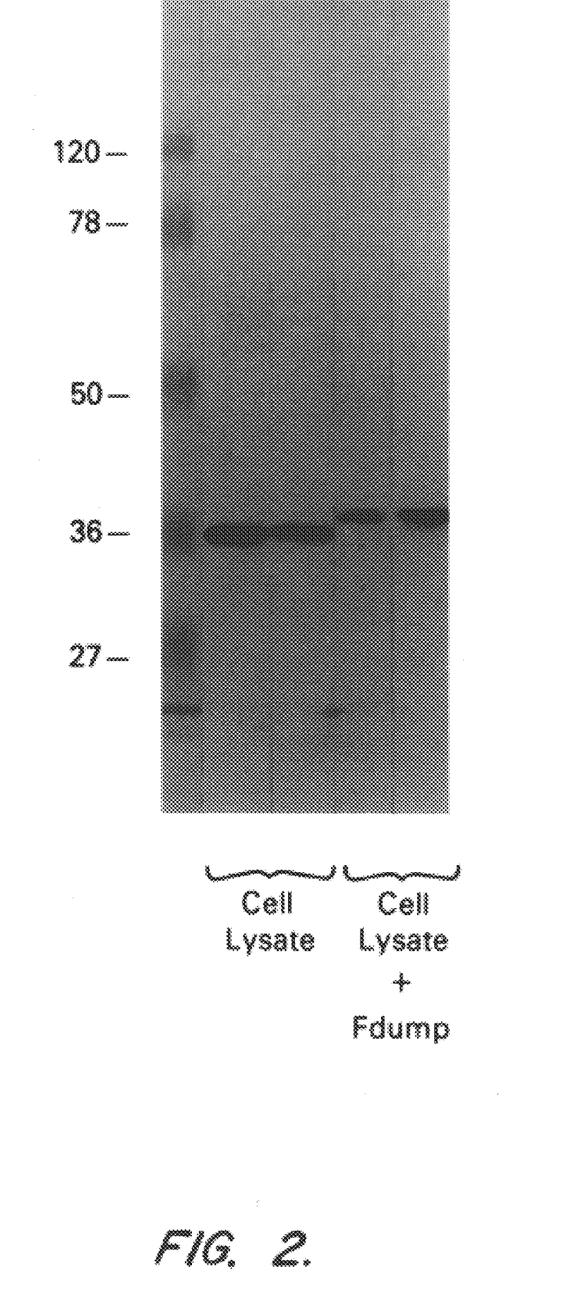
FIG. 2. A Western blot comparison of cell lysate from a human colon carcinoma cell lysate NIC $H630_{R10}$ that has been exposed to excess FdUMP (1 $\mu$m) and 5-10-methylene tetrahydrofolate (300 $\mu$m) and the same cell lysate that had not been exposes to excess folate of FdUMP. Lysates (100 $\mu$g) were resolved on SDS-polyacrylamide gels, transferred to nitrocellulose and stained with the monoclonal antibodies.
Figure 3:
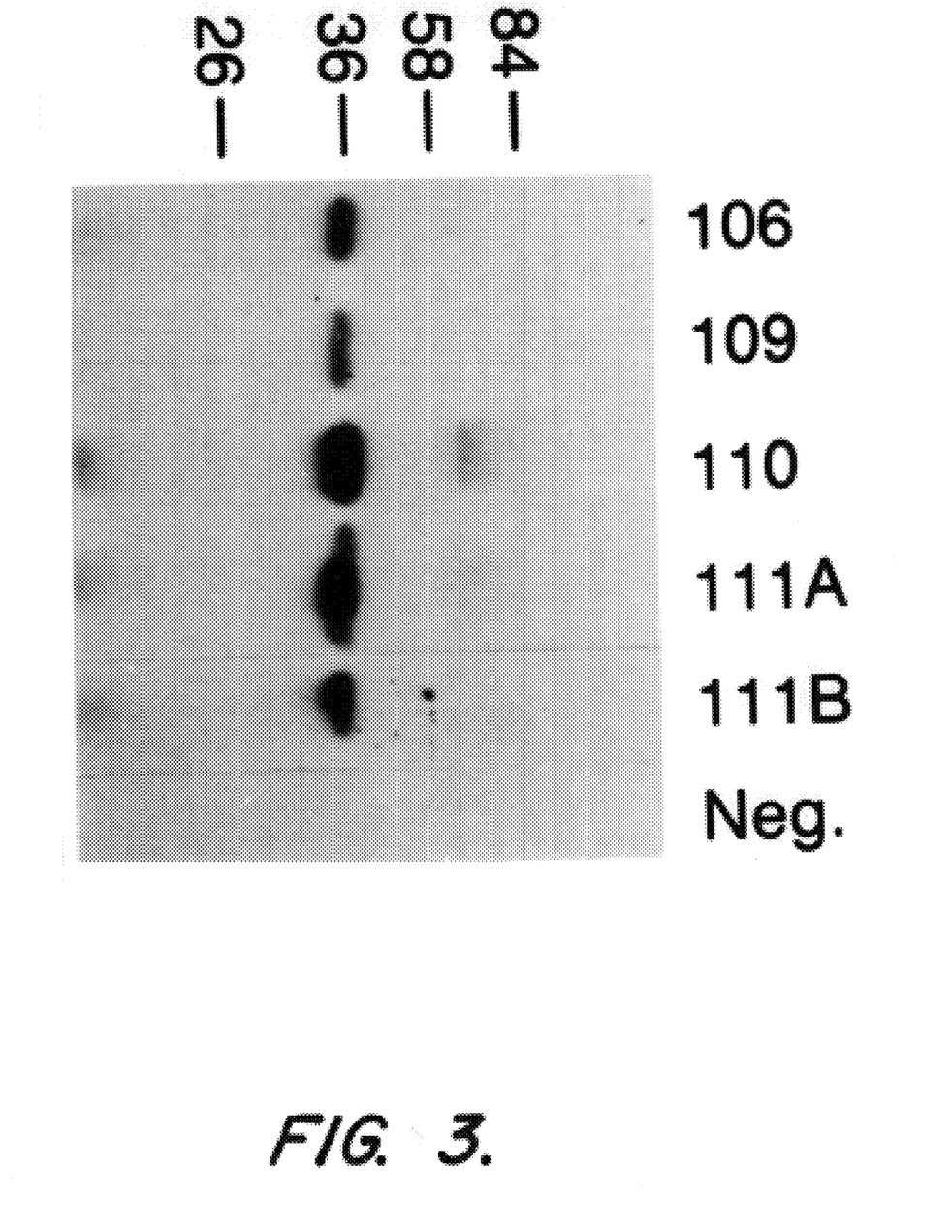
FIG. 3. Immunoprecipitation analysis of iodinated recombinant human TS using the monoclonal antibodies. A sample of each monoclonal antibody (10 $\mu$g/ml) was incubated overnight with protein A Sepharose. The protein Sepharose-conjugated monoclonal antibodies were incubated with iodinated rhTS and the resultant precipitates resolved on an SDS-polyacrylamide gel. The negative lane represents one of the monoclonals TS 109 preabsorbed with unlabeled rhTS prior to the incubation with iodinated rhTS. The gel was dried and autoradiographed.
Figure 4A:
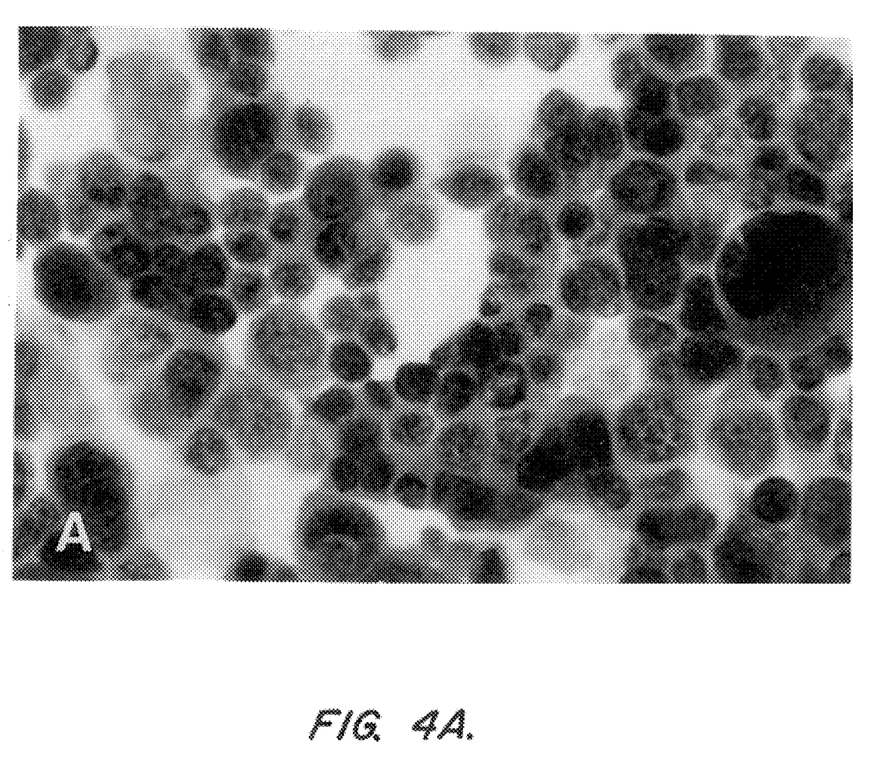
Figure 4B:
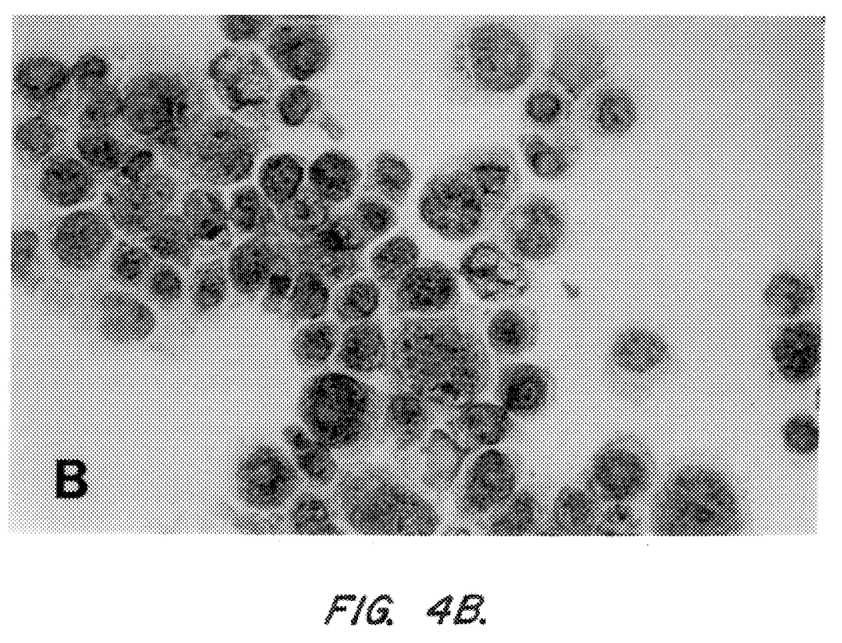
Figure 5A:
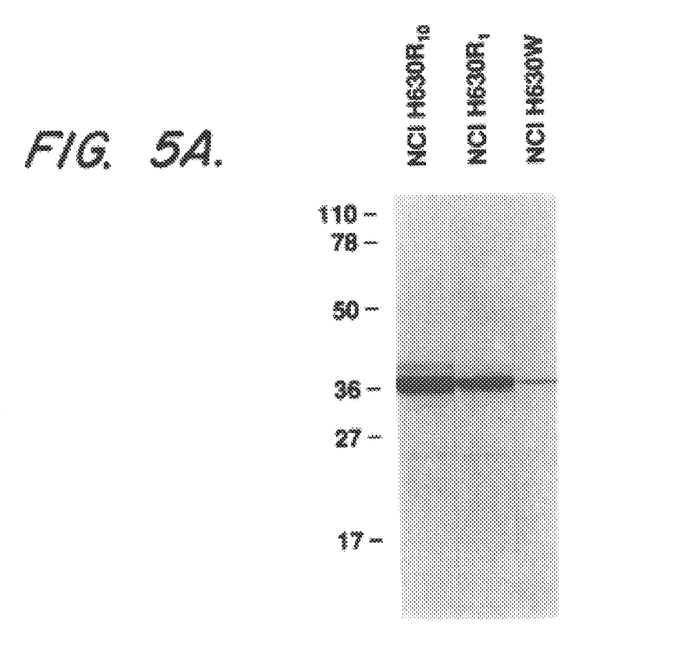
Figure 5B:
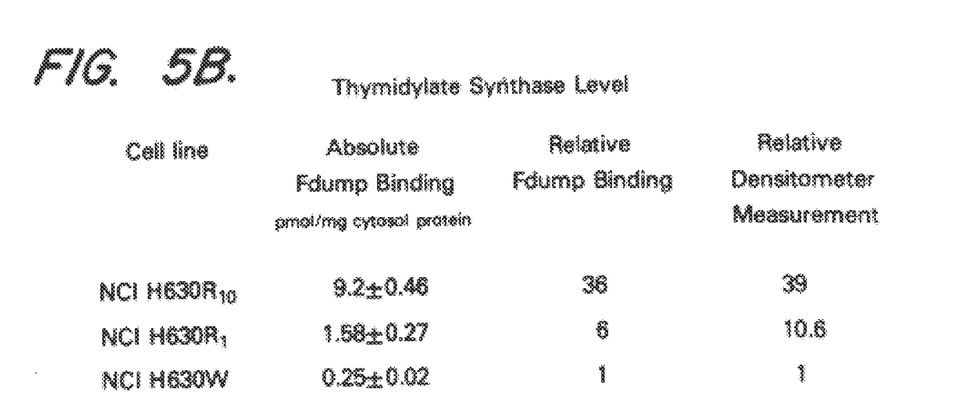
Figure 6A:
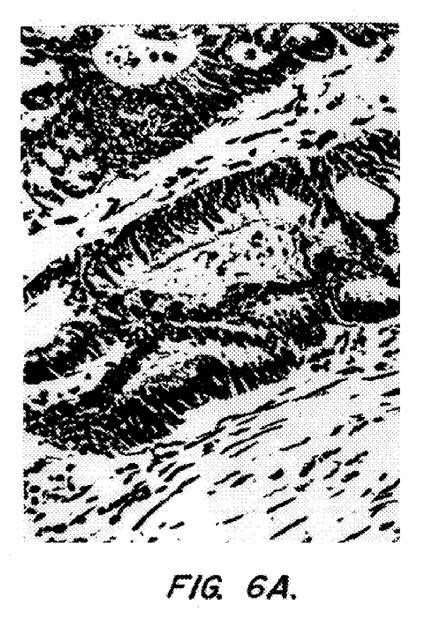
Figure 6B:
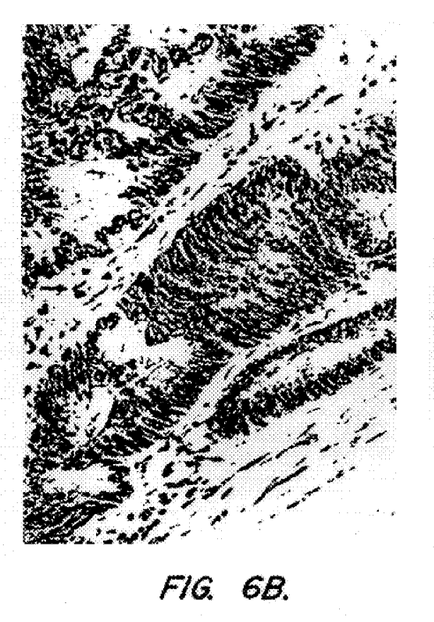
Figure 7:
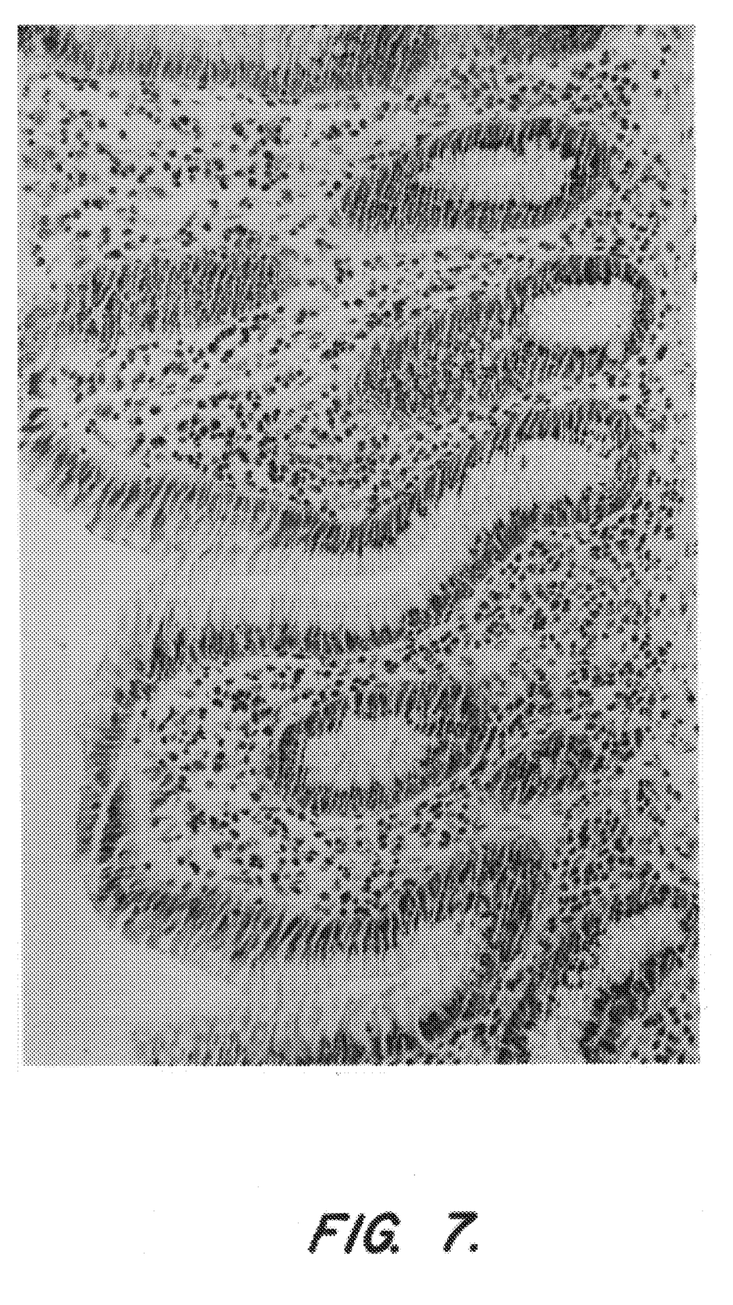
FIG. 7. Immunohistochemical staining using TS 106 in a biopsy sample of fresh-frozen normal colonic tissue. The tissue sample was processed as described for FIG. 5.

In these extracts the monoclonal antibodies specifically detected a peptide of 36 kD molecular weight and in addition displayed negligible cross-reactivity with other cellular peptides (FIG. 1, column A). Under non-reducing conditions, these antibodies also recognized the dimeric form of the TS peptide identifying a band at 72 kD. Western analysis of human colon carcinoma cell lysates that had been exposed to 10 $\mu$M 5-FU for 48 hours revealed that these antibodies detected two bands, the native TS peptide band at 36 kD and a band just above TS at approximately 38 kD. This upper band was not apparent in cells that had not been exposed to 5-FU, suggesting that this upper band represents the TS protein complexed to FdUMP and $CH_2H_4PteGlu$ (FIG. 1, column B). Thus it would appear that these antibodies are capable of recognizing both the free enzyme and the tight-binding covalent complex TS-FdUMP-$CH_2H_4PteGlu$ in human cells.

Mabs TS 106, TS 109, TS 110, and TS 111A, recognized the human T.S. dimeric peptide molecular weight 36 KD and 72 KD respectively from human colon carcinoma cell lysates. The reactivity of these antibodies with human T.S. from cell lysates on western analysis was not as strong as that with the T.S. peptide. This difference in reactivity may be explained by a lower affinity for the human T.S. or specific epitopes recognized by these antibodies may be more accessible or more stable in the r T.S. peptide. In addition to reacting with human T.S. Mabs, TS 106 and TS 109 cross reacted with Pneumocystis T.S. on ELISA.

In these extracts the monoclonal antibodies detected a dimeric peptide with migrating bands at 35 kD and 72 kD. However, the signal was much less intense than that noted with the r T.S. peptide. This was felt to be related to the overall concentration of T.S. peptide.

Immunoprecipitation

NCI-H630 colon carcinoma cells insert reframe #29 were plated onto T75 flasks (Falcon Labware) and maintained in RPMI plus 10% Fetal Calf Serum (FCS) and 2 mm glutamine. After 5 days cells incubated in methionine free RPMI plus FCS 10% for 2 hours and then washed in cold PBS. Labeling was then performed for 2 hours with 100 MCi/ml [$^{35}$S] methionine (sp/act 1000 Ci/mmol). Cells were collected by scraping from the surface of the flasks and then washed twice in cold PBS and centrifuged 1200×5 minutes. Cell lysate was prepared by incubating cells in a cell lysis buffer (300 mm. Nacl, 50 mm Tris 1% Triton) and Protease inhibitors (0.1 mm PMSF+aprotinin 3.3 $\mu$g/ml+leupeptin 10 $\mu$g/ml). To assess [$^{35}$S] Methionine Incorporation 10 ul of lysate was precipitated onto 0.45 $\mu$m filter discs using 10% trichloroacetic acid (T.C.A.) and counted in a scintillation vial. Prior to use the cell lysate was precleared using protein A Sepharose column. T.S. antibodies were incubated with protein A sepharose overnight and then incubated with 200 ul of precleared cell lysate for 4 hours at 4° C. Protein A sepharose beads were then washed 5 times in washing buffer (0.1% triton, 300 mm Nacl, 50 mm Tris) and 100 ml of sample buffer (2% SDS, 5% 2ME, 0.002% BPB in washing buffer) was added. This mixture was heated at 95° C. for 10 minutes and spun in a microfuge for 5 minutes at 14,000×g. Then 100 $\mu$l of the supernatant containing immune complex was loaded and analyzed by 15% SDS polyacrylamide gel electrophoresis. The radiolabeled proteins were visualized by exposure to Kodak X-RP film at −70° C. for five days.

Immunoprecipitation studies of the iodinated r T.S. peptide revealed that all antibodies were easily able to precipitate the 36 kD peptide. Preincubation of the Mabs with r T.S. blocked all reactivity on ELISA/Western blotting and immunoprecipitation, while preincubation of the monoclonal antibodies with albumin had in effect. Thus antibodies TS 106, TS 109, TS 110, TS 111A, and TS111B displayed strong reactivity with rTS and with a 36 KD protein from cellular extract from human colon cell lines on Western analysis and immunoprecipitation studies.

EXAMPLE 4

Immunocytological Assay of T.S. Enzyme: Comparison to Biochemical Fdump Binding Assay and Western Blot Assay Thymidylate Synthase Binding Assay NCI-H630 human colon cells were incubated in 5-FU at various drug concentrations and were harvested and resuspended in 0.1 m $K_2PO4$ pH 7.4. An aliquot of cells was processed for immunocytochemistry as described below. Cell lysis was accomplished by sonication using three 2–3 second bursts. The cellular extract was centrifuged at 10,000 g×30 minutes and the supernatants collected and assayed. The formation of complex (T.S.-Fdump ($CH_2$—$H_4$Pte Glu) was calculated by measuring total Fdump binding sites (T.S. total) and unoccupied Fdump binding sites T.S. free ($TS_f$). The difference between these was the T.S. bound ($TS_b$). The T.S. free was quantitated by adding 20 ul of cell lysate to 180 ul containing (5 Fdump (18 Ci/mmol), 100 mm Mercaptoethanol and 50 mm $KH_2PO_4$PH 7-2). Samples were incubated at 37° C. for 30 minutes. Following this free Fdump was removed by the addition of activated Charcoal 100 ml (albumin 2.5 mg/ml T-70 dextran treated 3% activated Charcoal in 0.1 N HCL) and subsequent centrifugation (10,000 g×30 minutes) 800 ml of supernatant was counted using a liquid scintillation counter. T.S. total was determined by allowing $TS_B$ present in the cytosol to fully exchange with labelled Fdump in 0.6 M $NH_4HCO_3$ (pH 8.0) buffer over a 3 hour time period (Spears et al., Cancer Res. 1982 42:450–456).

Immunohistochemistry

NCI-H630 colon carcinoma cells were plated onto in T 75 flasks (Falcon Labware) and harvested during the exponential part of the growth phase, i.e., on day 5 after plating. Cytospin preparations were made on glass slides using a Shandon cytocentrifuge. The cells were fixed in acetone for 10 minutes at room temperature. The slides were subsequently rinsed in P.B.S. and incubated with normal horse serum (2% in P.B.S.) for 30 minutes to reduce non-specific staining. The cells were then incubated with monoclonal antibody (20 ug/ml) or with normal mouse IgG (10 ug/ml) for 4 hours at room temperature. Cells were rinsed in P.B.S. for 10 minutes and 50 ul of an avidin biotin-conjugated antimouse secondary antibody was added for 30 minutes. Cells were once again rinsed in P.B.S. and incubated with A.B.C. complex (Vector Laboratories) for 30 minutes. After a final rinsing in P.B.S. the cells were incubated with D.A.B. substrate (0.02% D.A.B., 0.005% hydrogen peroxidase) for 15 minutes (insert reframe #30 Hsu et al., J Histochem Cytochem 1981 29:577–580; Hsu et al., J Clin Pathol 1981 75:734–738). The cells were then counterstained in hematoxylin and mounted.

Immunohistochemical Staining

Colon carcinoma tissue specimens were placed in O.C.T. compound and frozen in dry ice/acetone. Tissue sections 6 um thick were cut in a cryostat and mounted on poly-1-lysine-4 coated slides. Slides were immersed in 3% normal goat serum for 30 minutes at room temperature. Sections were then incubated with affinity purified antibody (20 ug/ml) for 4 hours. The tissue was then washed in P.B.S. and incubated successively with avidin-biotin labelled anti-mouse antibody and, A.B.C. solution (Vector Laboratories) and D.A.B. substrate solution as outlined above.

Evaluation of Immunocytochemical Staining

Two MoAbs, TS 106 and TS 109, displayed strong cytochemical staining of cytopreps from several human colon carcinoma cell lines. The pattern of reactivity was a dark granular appearance diffusely spread throughout the cytoplasm. The specificity of staining was demonstrated by disappearance of the granular pattern when the MoAbs were preincubated with rhTS prior to application to the colon carcinoma cells. The staining appeared to be confined to the cytoplasm and the intensity and number of stained cytoplasmic granules varied among the cell lines studied.

In an effort to demonstrate that the immunocytochemical detection of TS is a sensitive and quantitative method of detecting human TS, a direct comparison of immunocytochemical analysis, Western blotting and biochemical TS assays was carried out using 5-FU-sensitive and -resistant H630 colon carcinoma cell lines. Western analysis using MoAbs 106 and 109 revealed a dramatic increase in the level and intensity of the TS band in the H630-resistant cell line compared to the sensitive H630 line. Based on densitometric quantitation, a 56-fold increase in the TS level was present in the resistant as compared to the sensitive NCI-H630 cell line. A similar increase in the number and staining intensity of TS cytoplasmic granules was detected by immunohistochemical staining. This increase in staining TS as demonstrated by immunohistochemistry paralleled the 44-fold increase in TS enzyme as measured by the FdUMP binding assay (Table 3). These data suggest that an immunoperoxidase or immunofluorescence assay may be a useful and accurate method for quantitation of TS in human cancer cell lines.

To determine whether these antibodies would recognize T.S. in human biopsy specimens, sections 6 micron thick of fresh frozen colorectal carcinoma tissue were studied. Monoclonal antibodies TS 106 and TS 109 displayed strong histochemical staining. The staining pattern was considered specific for the T.S. enzyme because it was not observed with pre-immune IgG and a marked reduction in staining intensity in background levels occurred when the antibody was absorbed with recombinant T.S. peptide. On light microscopic examination the staining pattern was a granular cytoplasmic appearance as previously noted in colon cell lines. The granular staining was predominantly noted in the tubular and cribriform glands of colorectal cancers as well as a subset of lymphocytes located within the tumor samples. Minimal cross reactivity with smooth muscle and red blood cells was also observed, and could be absorbed out by preincubation of monoclonal antibodies with rTS. Of particular note, the staining intensity was greater in the higher grade less differentiated tumors while in the more differentiated tumors staining was weak or absent. In normal colonic crypts and glands positively staining cells were rare and staining intensity was much less than that observed in coloreactal tumors.

Immunocytochemical staining of human colon carcinoma cell lines H630, H568, C1, with Mabs TS 106 and TS 109 produced a positive granular cytoplasmic staining pattern. The specificity of this T.S. antibody interaction was confirmed by loss of reactivity when the antibody was preincubated with purified r T.S. peptides. Thus these antibodies are capable of detecting and localizing human T.S. in the cytoplasma of colon carcinoma cells. A comparison of the immunolabeling of T.S. and the biochemical Fdump (radiolabelled) binding T.S. assay revealed that in those cells with higher T.S. levels there were a greater number of cytoplasmic granules present and the staining was stronger. In addition, acute rises in cellular T.S. could be detected when H630 cells were exposed to 5 Fluorouracil. Thus it would appear that by using an immunocytochemical assay these antibodies may accurately detect changes in the amount of T.S. present within individual cells.

A granular cytoplasmic staining pattern was noted in the malignant glands, and the high grade more undifferentiated tumors stained more intensely. Sections of normal colonic tissue adjacent to the malignant tumor exhibited little or no staining. Thus we have shown that TS 106 and TS 109 may be used to localize T.S. in human tissue. These antibodies may also help to quantitate the level and determine the clinical significance of T.S. in various human tumors.

The foregoing invention has been described in some detail by way of examples for purposes of clarity and understanding. It will be obvious to those skilled in the art from a reading of the disclosure that various combinations in form and detail can be made without departing from the scope of the invention. It will also be clear to those skilled in the art that the antibodies of the invention can be used to isolate the antigens for which they are specific.

The entire contents of all references cited herein above are hereby incorporated by reference.

TABLE 1

COMPARISON OF ANTIBODY ISOTOPE BINDING USING LABELED AND UNLABELED ANTIBODIES

| Unlabeled Antibody | Labeled Monoclonal Antibodies (Optical Density Units) | | |
| --- | --- | --- | --- |
| | TS 106 | TS 109 | TS 111A |
| TS 106 | 0.032 | 0.036 | 1.446 |
| TS 109 | 0.027 | 0.03 | 0.062 |
| TS 110 | 0.056 | 0.047 | 1.29 |
| TS 111A | 1.56 | 0.52 | 0.027 |

TABLE 2

ANTIBODY CHARACTERISTICS

| Antibody | Isotype | ELISA Titer | rhTS[1] | | Human TS[2] | | |
| --- | --- | --- | --- | --- | --- | --- | --- |
| | | | West[4] | Ippt[5] | West | Ippt | IHC[3] |
| Ts 106 | IgG$_1$ | ≧100,000 | + | + | + | + | + |
| Ts 109 | IgG$_1$ | ≧100,000 | + | + | + | + | + |
| Ts 110 | IgG$_1$ | ≧100,000 | + | + | + | + | +/− |
| Ts 111A | IgG$_1$ | ≧100,000 | + | + | + | + | − |
| Ts 111B | IgM | ≧100,000 | + | + | + | + | − |

[1]rhTS = recombinant human thymidylate synthase
[2]Human TS = thymidylate synthase from human colon carcinoma cells
[3]IHC = immunohistochemistry
[4]West = Western blot analysis
[5]Ippt = immunoprecipitate

TABLE 3

THYMIDYLATE SYNTHASE IN A SENSITIVE AND RESISTANT
HUMAN COLON CARCINOMA CELL LINE (NCI-H630)

| Cell Line | FdUMP Binding Assay (pmol/mg) |
|---|---|
| Sensitive | 0.16 ± 0.03 |
| Resistant | 7.0 ± 0.24 |

What is claimed is:

1. A hybridoma that produces a monoclonal antibody specific for an antigenic determinant of thymidylate synthase, said antibody with sufficient binding affinity to detect thymidylate synthase in a Western blot assay.

2. The hybridoma according to claim 1 resulting from the fusion of a myeloma cell and a spleen cell.

3. The hybridoma according to claim 2 wherein said myeloma cell is derived from a mouse.

4. The hybridoma according to claim 2 wherein said spleen cell is derived from a mammal immunized with human thymidylate synthase.

5. The hybridoma according to claim 4 wherein said mammal is a mouse.

6. A monoclonal antibody, or binding fragment thereof, specific for an antigenic determinant of thymidylate synthase, said antibody with sufficient binding affinity to detect thymidylate synthase in a Western blot assay.

7. The monoclonal antibody according to claim 6 wherein said antibody is of the IgM class or the IgG class.

8. A diagnostic kit comprising in combination at least one monoclonal antibody according to claim 6 and an ancillary reagent.

9. The diagnostic kit according to claim 8 that contains an insoluble surface or support containing microtiter wells.

10. The diagnostic kit according to claim 9 that contains thymidylate synthase or antigenic fragments thereof, which are bound to said support.

11. A method of determining the presence of thymidylate synthase in a biological sample, comprising:

i) contacting said sample with at least one monoclonal antibody specific for an antigenic determinant of thymidylate synthase, under conditions such that binding of such monoclonal antibody to said antigenic determinant occurs, and ii) detecting the presence or absence of complex formed between said monoclonal antibody and said antigenic determinant, said antibody with sufficient binding affinity to detect thymidylate synthase in Western blot assay.

12. The method of claim 11 wherein said biological sample comprises tumor cells.

13. The method of claim 12 wherein said tumor cells include carcinoma cells.

14. The method of claim 13 wherein said carcinoma cells are derived from a colon.

15. The method of claim 11 wherein said biological sample is taken from a human.

16. The method of claim 11 further comprising quantifying an amount of complex formed.

17. The method of claim 11 wherein the steps of contact and detection are appropriate to a member selected from the group of assay formats consisting of an immunohistochemical assay, an ELISA, a Western blot assay, and an immunoprecipitation assay.

18. The method of claim 11 wherein said sample comprises denatured thymidylate synthase.

19. The method of claim 11 wherein said antibody is selected from a group consisting of TS 106, TS 109, TS 110, and TS 111A.

20. The monoclonal antibody of claim 6 wherein said antibody is TS 106.

* * * * *

UNITED STATES PATENT AND TRADEMARK OFFICE
CERTIFICATE OF CORRECTION

PATENT NO. : 6,221,620 B1
DATED : April 24, 2001
INVENTOR(S) : Johnston et al.

It is certified that error appears in the above-identified patent and that said Letters Patent is hereby corrected as shown below:

Column 16, claim 19,
Line 33, please delete "selected from a group consisting of".
Lines 33-34, please delete "TS 109, TS 110, and TS 111A".

Signed and Sealed this

Twenty-second Day of January, 2002

Attest:

Attesting Officer

JAMES E. ROGAN
*Director of the United States Patent and Trademark Office*